United States Patent
Franczyk, II

(10) Patent No.: US 7,294,733 B2
(45) Date of Patent: *Nov. 13, 2007

(54) METHOD FOR PREPARING FORMYLPHOSPHONIC ACID

(75) Inventor: Thaddeus S. Franczyk, II, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/422,256

(22) Filed: Jun. 5, 2006

(65) Prior Publication Data

US 2006/0211881 A1 Sep. 21, 2006

Related U.S. Application Data

(63) Continuation of application No. 10/868,236, filed on Jun. 15, 2004, now Pat. No. 7,091,376, which is a continuation of application No. 10/236,626, filed on Sep. 4, 2002, now Pat. No. 6,762,317, which is a continuation of application No. 09/835,450, filed on Apr. 16, 2001, now abandoned, which is a continuation of application No. 09/556,341, filed on Apr. 24, 2000, now Pat. No. 6,218,570, which is a continuation of application No. 09/071,265, filed on May 1, 1998, now Pat. No. 6,054,608.

(60) Provisional application No. 60/045,825, filed on May 5, 1997.

(51) Int. Cl.
*C07F 9/22* (2006.01)
*C07F 9/30* (2006.01)
*C07F 9/32* (2006.01)

(52) U.S. Cl. .................... 558/137; 558/144; 562/8; 562/17; 562/24

(58) Field of Classification Search ........... 562/8, 562/17, 24; 558/137, 144
See application file for complete search history.

(56) References Cited

U.S. PATENT DOCUMENTS

| | | |
|---|---|---|
| 3,738,937 A | 6/1973 | Kautsky |
| 3,784,590 A | 1/1974 | Firestone |
| 3,907,652 A | 9/1975 | Wagenknecht et al. |
| 3,969,398 A | 7/1976 | Hershman |
| 4,072,706 A | 2/1978 | Hershman et al. |
| 4,264,776 A | 4/1981 | Hershman et al. |
| 4,348,332 A | 9/1982 | Oediger et al. |
| 4,439,474 A | 3/1984 | Sagel |
| 4,568,432 A | 2/1986 | Rogers |
| 4,624,937 A | 11/1986 | Chou |
| 4,657,705 A | 4/1987 | Miller et al. |
| 6,232,494 B1 | 5/2001 | Morgenstern |
| 6,762,317 B2 * | 7/2004 | Franczyk, II ............... 562/17 |
| 7,091,376 B2 * | 8/2006 | Franczyk, II ............... 562/24 |

* cited by examiner

*Primary Examiner*—Peter O'Sullivan
(74) *Attorney, Agent, or Firm*—Senniger Powers; Joseph A. Shaper

(57) ABSTRACT

An improved process for the manufacture of formylphosphonic acid derivatives is reported. An aminomethylphosphonic acid substrate is contacted with a reagent selected from the group consisting of water, an alcohol, a phenol compound, and mixtures thereof and an oxidizing gas in the presence of a catalyst to form a reaction product mixture containing a formylphosphonic acid derivative and the conditions under which said contacting is carried out are controlled so that no more than 50% of the formylphosphonic acid derivative formed in the reaction product mixture is consumed by reaction with the reagent.

20 Claims, 1 Drawing Sheet

METHOD FOR PREPARING FORMYLPHOSPHONIC ACID

This application is a continuing patent application of prior Ser. No. 10/868,236 (filed Jun. 15, 2004), now U.S. Pat. No. 7,091,376, which is a continuation of prior Ser. No. 10/236, 626 (filed Sep. 4, 2002), now U.S. Pat. No. 6,762,317, which issued as U.S. Pat. No. 6,762,317 on Jul. 13, 2004, which is a continuing patent application of prior Ser. No. 09/835,450 (filed Apr. 16, 2001), now abandoned, which is a continuing patent application of prior Ser. No. 09/556,341 (filed Apr. 24, 2000), which issued as U.S. Pat. No. 6,218,570 on Apr. 17, 2001, which is a continuation of prior Ser. No. 09/071, 265 (filed May 1, 1998), which issued as U.S. Pat. No. 6,054,608 on Apr. 25, 2000, which is a non-provisional of U.S. Provisional Application No. 60/045,825 (filed May 5, 1997).

BACKGROUND OF THE INVENTION

1. Field of the Invention

This invention relates to the preparation of formylphosphonic acid derivatives and particularly to novel processes for the preparation of formylphosphonic acid, its salts, esters, hydrate, acetals, and hemiacetals by the catalytic oxidation of aminomethylphosphonic acid derivatives.

2. Description of Related Art

Phosphorus-containing compounds such as formylphosphonic acid are important precursors for the synthesis of organophosphorus compounds. Such organophosphorus compounds have numerous applications. For example, formylphosphinic acid can be used as a precursor in the synthesis of N-(phosphonomethyl)glycine, a highly effective commercial herbicide (available under the trade name Roundup®) useful for the control of a large variety of weeds. Formylphosphonic acid can alternatively be used as an advanced intermediate in the preparation of medicinally important compounds such as the antiviral agent phosphono hydroxyacetic acid. As a reagent or intermediate, formylphosphonic acid has potential for chemical transformation at the carbonyl, phosphorus, or hydroxyl moieties.

Researchers have reported electrochemical processes in which formylphosphonic acid forms. For example, Wagenknecht (Synth. React. Inorg. Met.-Org. 4:567-572 (1974)) spectrophotometrically observes or isolates formylphosphonic acid in the electrochemical oxidation of nitrilotris(methylenephosphonic acid) to the secondary amine. A similar reaction is reported in U.S. Pat. No. 3,907,652. In J. Electrochem. Soc. 123:620-624 (1976) Wagenknecht reports the electrochemical oxidation of substituted iminodimethylenediphosphonic acids to produce the secondary amine. In that study, formylphosphonic acid was isolated in unreported yield as a side product. Wagenknecht, et al. again reports the formation of formylphosphonic acid as a side product in the electrochemical oxidation of nitrilotris(methylene-phosphonic acid) in Synth. React. Inorg. Met.-Org. 12:1-9 (1982). However, these reactions suffer from several shortcomings. Yields of formylphosphonic acid are poor or unreported. The reaction requires the addition of a strong hydrochloric acid solution which presents safety, environmental, and equipment corrosion problems. Electrochemical methods generally require an external power source and other equipment which typically have higher maintenance needs and costs than do non-electrochemical reactions. It would be advantageous to have a method for the preparation of formylphosphonic acid in high yield which does not require specialized electrochemical equipment and does not require the handling of large quantities of strong mineral acids.

Hershman et al., in U.S. Pat. No. 4,072,706, disclose a process in which tertiary phosphonomethylamines are oxidized with oxygen, in the presence of an activated carbon catalyst, to cleave a phosphonomethyl group and produce a secondary amine. According to Hershman et al., formylphosphonic is produced as an intermediate cleavage fragment, with the fragment undergoing hydrolysis in a second step to formic acid and phosphorous acid. Hershman et al., however, identify formylphosphonic acid as an intermediate cleavage fragment in only one reaction run and although the yield is unreported it is apparently low. In addition, Hershman et al. fail to disclose any means to reduce the hydrolysis of the intermediate cleavage fragment.

Thus, a need exists for a convenient, environmentally-compatible, safe, and cost-effective process for the oxidative cleavage of aminomethyl-phosphonic acid derivatives to produce formylphosphonic acid in high yield with minimal degradation.

SUMMARY OF THE INVENTION

To address this and other needs, an improved process for the manufacture of formylphosphonic acid derivatives is now reported. Among the several objects of the present invention is an improved process for the manufacture of formylphosphonic acid, its esters, salts, acetals, hemiacetals, and hydrate.

Briefly, therefore, one aspect of the present invention is directed to a process for the preparation of formylphosphonic acid, its esters, salts, acetals, hemiacetals, and hydrate, especially of formylphosphonic acid, wherein the process comprises contacting an aminomethylphosphonic acid substrate, a reagent selected from the group consisting of water, an alcohol, a phenol compound, and mixtures thereof and an oxidizing gas in the presence of a catalyst to form a reaction product mixture containing a formylphosphonic acid derivative. In the process, the conditions under which said contacting is carried out are controlled so that no more than 50% of the formylphosphonic acid derivative formed in the reaction product mixture is consumed by reaction with the reagent.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will from this detailed description become apparent to those skilled in the art.

DETAILED DESCRIPTION OF THE INVENTION

Figure 1:
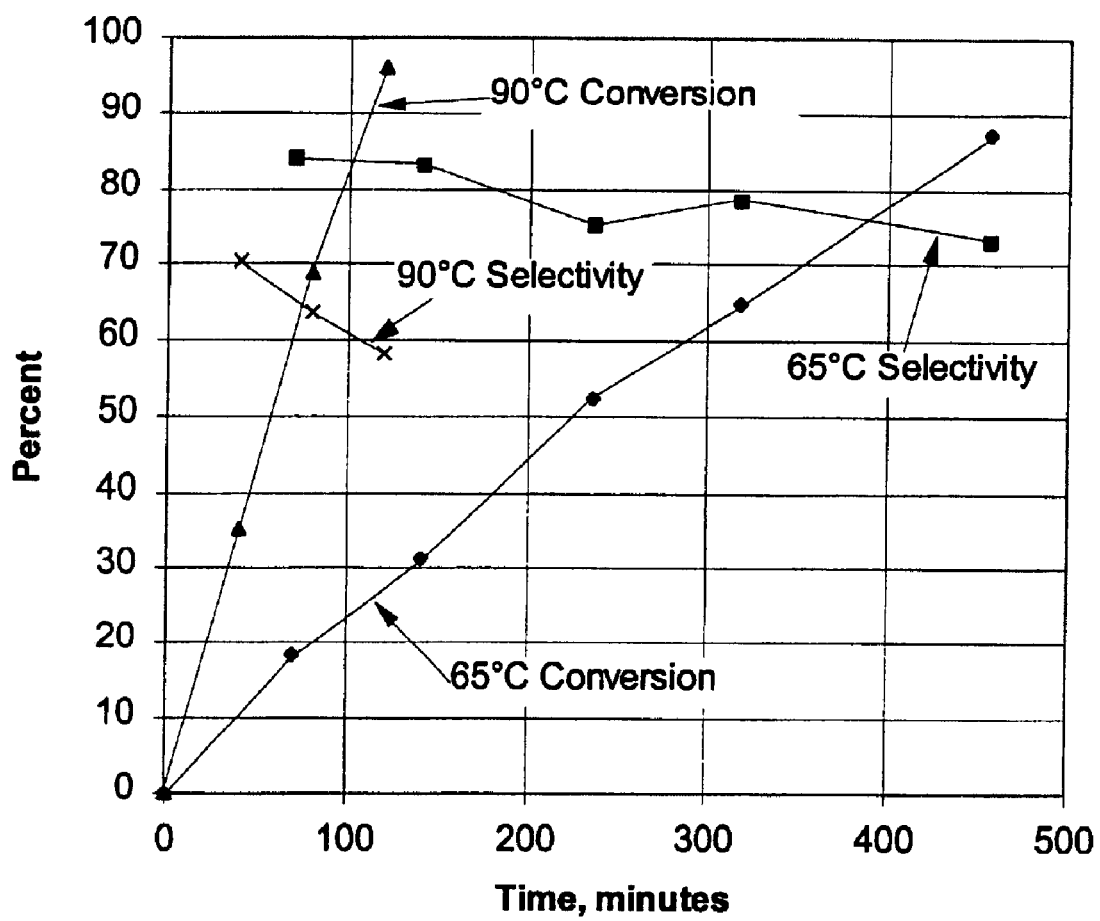
FIG. 1 shows the effect of temperature on conversion and formylphosphonic acid selectivity where nitrilotris(methylenephosphonic acid) is used as the starting material under the conditions of the invention. The underlying data for FIG. 1 is shown in Table 2.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

Definitions

The following definitions are provided in order to aid the reader in understanding the detailed description of the present invention:

"Hydrocarbyl" means a group composed of carbon and hydrogen. This definition includes alkyl, alkenyl, and alkynyl groups which are each straight chain, branched chain, or cyclic hydrocarbons from one to about twenty carbons. Also included in this definition are aryl groups composed of carbon and hydrogen. Hydrocarbyl therefore includes, for example, methyl, ethyl, propyl, butyl, pentyl, hexyl, cyclopropyl, cyclobutyl, cyclopentyl, cyclohexyl, methylcyclopentyl, ethenyl, propenyl, butenyl, pentenyl, hexenyl, ethyne, propyne, butyne, pentyne, hexyne, phenyl, naphthyl, anthracenyl, benzyl, and isomers thereof.

"Substituted hydrocarbyl" means a hydrocarbyl group in which one or more hydrogen has been substituted with a heteroatom-containing group. Such substituent groups include, for example, halo, oxo, heterocycle, alkoxy, hydroxy, aryloxy, —$NO_2$, amino, alkylamino, or amido. When the substituent group is oxo, the substituted hydrocarbyl can be, for example, an acyl group.

"Heteroatom" means an atom of any element other than carbon or hydrogen which is capable of forming chemical bonds.

"Heterocycle" means a saturated or unsaturated mono- or multi-ring carbocycle wherein one or more carbon atoms is replaced by N, S, P, or O. This includes, for example, the following structures:

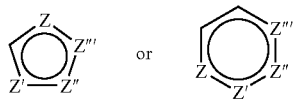

wherein Z, Z', Z", or Z'" is C, S, P, O, or N, with the proviso that one of Z, Z', Z", or Z'" is other than carbon, but is not O or S when attached to another Z atom by a double bond or when attached to another O or S atom. Furthermore, the optional substituents are understood to be attached to Z, Z', Z", or Z'" only when each is C. The point of attachment to the molecule of interest can be at the heteroatom or elsewhere within the ring.

"Halogen" or "halo" means a fluoro, chloro, bromo, or iodo group.

"Pyrolyze" means to break apart molecules into smaller units by the use of heat.

"Oxidizing gas" means a gas or a gas mixture which comprises an oxidant. Oxidants can include, for example, $O_2$, nitrogen oxides, singlet oxygen and ozone.

"Oxygen atom-containing gas" means a gas or a gas mixture in which one or more of the components comprises an oxygen atom.

"Surface oxide" means a reactive group on the surface of activated carbon, which reactive group comprises one or more oxygen atoms.

"GC" means gas chromatography.
"HPLC" means high pressure liquid chromatography.
"IC" means ion chromatography.
"NMR" means nuclear magnetic resonance spectroscopy.
"MS" means mass spectrometry.

Process Details

In accordance with the present invention, a formylphosphonic acid derivative having the formula (I) can surprisingly be obtained in high yield by the reaction of an aminomethylphosphonic acid substrate with an oxidant and a reagent (water, an alcohol, a phenol compound or a mixture thereof) in a reaction mixture in the presence of a catalyst. The reaction is conducted under conditions at which preferably at least about 25%, more preferably at least about 50%, and still more preferably at least about 75% of said substrate is oxidized to produce formylphosphonic acid without consuming more than 50% of the formylphosphonic so produced by reaction with said reagent. Broadly, this reaction is shown in Eq. 1, wherein the aminomethylphosphonic acid substrate has formula (II), $R^1$ and $R^2$ can independently be H, hydrocarbyl, substituted hydrocarbyl, a salt-forming cation, and heterocycle; $R^3$ can be —CHO, or —CH($OR^8$)($OR^9$); $R^4$ and $R^5$ can independently be H, —$CH_2PO(OR^6)(OR^7)$, hydrocarbyl, substituted hydrocarbyl, and heterocycle; $R^6$ and $R^7$ can independently be H, hydrocarbyl, substituted hydrocarbyl, a salt-forming cation and heterocycle; and $R^8$ and $R^9$ can independently be H, hydrocarbyl, substituted hydrocarbyl, and heterocycle.

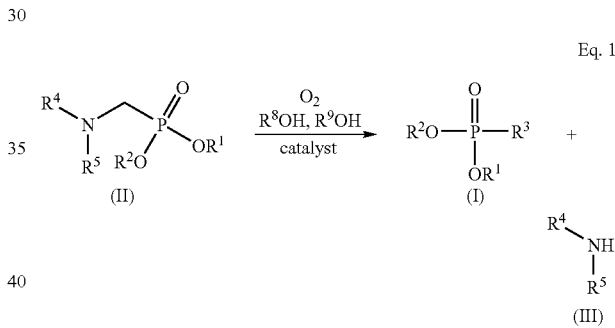

Eq. 1

Surprisingly, it has been discovered that the degradation of formylphosphonic acid to formic acid and phosphorous acid can be controlled through the selection of time and temperature. In general, the rate of degradation of formylphosphonic acid to formic acid and phosphorous acid increases with increasing time and temperature with the rate of increase for this reaction step being greater than the rate of increase for the conversion of aminomethylphosphonic acid to formylphosphonic acid. Accordingly, the time and temperature of reaction are controlled so that the molar ratio of formylphosphonic acid (or derivative thereof) to formic acid is at least about 1:1, more preferably at least about 2:1, and optimally at least about 3:1.

Although the reaction may be carried out at temperatures in the range of 150° C., at this temperature the degradation of formylphosphonic acid would proceed at such a rate that it would be difficult to obtain a significant yield of formylphosphonic acid. In general, therefore, it is preferred that the reaction be carried out a temperature of less than 115° C., more preferably at a temperature of less than 95° C., and still more preferably at a temperature not in excess of 85° C. In addition, for any period of time in which about 75% or more of the formylphosphonic acid derivative is formed, the reaction time is preferably less than about 120 minutes for reaction temperatures greater than about 105° C., preferably less than about 5 hours for reaction temperatures between about 95° C. and about 105° C., preferably less than about 15 hours for reaction temperatures between about 85° C. and about 95° C. and preferably tens of hours or greater (e.g., about 20 to about 30 hours or more) for reaction temperatures less than about 85° C.

In general, the reaction mixture preferably contains at least one equivalent of a reagent selected from the group consisting of water, an alcohol, a phenol, or mixtures thereof for each equivalent of formylphosphonic acid desired as a reaction product. The alcohol may be any of a broad class of hydroxyl-containing organic compounds including, for example, monohydric, dihydric, or polyhydric compounds which are otherwise hydrocarbyl, substituted hydrocarbyl, or heterocyclic. Similarly, the phenol may be any of a class of aromatic compounds in which one or more hydroxy groups are attached directly to the aromatic ring. Examples include benzophenol, the cresols, xylenols, resorcinol, naphthols, etc.

The catalyst is generally any material effective at catalyzing the formation of formylphosphonic acid derivatives according to the inventive method. The catalyst can be a heterogeneous catalyst or a homogeneous catalyst. For the purposes of this invention, the term "homogeneous catalyst" refers to a catalyst which is soluble in the reaction mixture. The term "heterogeneous catalyst" refers to a catalyst which is insoluble or substantially insoluble in the reaction mixture. The term "reaction mixture" includes reaction mixtures which contain one discrete phase and reaction mixtures which contain more than one discrete phase. Examples of reaction mixtures which contain more than one discrete phase include oil-in-water emulsions and water-in-oil emulsions.

Typically the reaction mixture for this process can be neutral or acidic and generally contains a Lewis acid such as HCl or $AlCl_3$. If water is used as the solvent, the pH is less than about 6, more preferably less than about 3, and most preferably less than about 1.5. The reaction can be run in the presence of added base such as an alkali metal hydroxide, but it is preferred that if a base is added, such addition is less than one equivalent of base per equivalent of aminomethylphosphonic acid derivative. Data in Table 1 exemplify the effect of pH and added base on the yield of formylphosphonic acid (FPA, formula I, wherein $R^1$ and $R^2$ are H, and $R^3$ is —CHO) in the reaction of nitrilotris(methylenephosphonic acid) (formula (II) wherein $R^1$ and $R^2$ are H, and $R^4$ and $R^5$ are —$CH_2PO_3H_2$) in the process of this invention. Although Table 1 shows results obtained using a heterogeneous catalyst, the acid-dependence of the present invention is independent of the type of catalyst used.

TABLE 1

| Number of Equivalents of added Acid or Base | Product pH | Conversion at 120 minutes (%) | Maximum FPA Yield, % (at time in minutes) | Maximum NFI Yield, % |
|---|---|---|---|---|
| 1.0 eq. HCl | 0.9 | 97 | 69 (120) | 10 |
| none | 1.0 | 99 | 71 (120) | 5 |
| 1.0 eq. NaOH | 1.4 | 97 | 62 (120) | 17 |
| 1.8 eq. NaOH | 2.1 | 68 | 38 (120) | 20 |
| 2.2 eq. NaOH | 2.9 | 65 | 28 (120) | 30 |

TABLE 1-continued

| Number of Equivalents of added Acid or Base | Product pH | Conversion at 120 minutes (%) | Maximum FPA Yield, % (at time in minutes) | Maximum NFI Yield, % |
|---|---|---|---|---|
| 3.0 eq. NaOH | 4.5 | 94 | 14 (30) | 65 |
| 4.0 eq. NaOH | 5.9 | approx. 100 | 8 (60) | 63 |

Reaction conditions are described in Example 6.
FPA = formylphosphonic acid
NFI = N-formyliminobis(methylenephosphonic acid)

When a heterogeneous catalyst is employed in the present invention, the catalyst is preferably a carbon catalyst. Carbon catalysts which are particularly useful in the present invention can be prepared by the methods described in U.S. Pat. No. 4,624,937, which is herein incorporated by reference. The carbon catalyst can be produced by a method which comprises pyrolyzing activated carbon at a temperature in the range of about 500° C. to about 1500° C. while simultaneously contacting the activated carbon with a first gas comprising $NH_3$ and a second gas comprising an oxygen atom-containing gas wherein the weight ratio of the oxygen atom-containing gas to $NH_3$ is in the range of about 0:100 to about 90:10. The length of time during which the activated carbon is contacted with the first gas and the second gas must be sufficient in duration to remove surface oxides from the activated carbon. The oxygen atom-containing gas is preferably $H_2O$, a nitrogen oxide, $O_2$, $CO_2$, $SO_2$, or a mixture thereof. Preferably, the oxygen atom-containing gas is $H_2O$.

Alternatively, the carbon catalyst can be from the Norit class of activated carbons, commercially available from American Norit Company (Jacksonville, Fla.). Preferred Norit carbon catalysts are Norit SX Plus or Norit SA-3.

The heterogeneous catalyst employed in the present invention can comprise carbon impregnated with a noble metal. Preferably the noble metal is platinum or palladium and most preferably it is platinum.

In the presence of a heterogeneous catalyst, the process of the present invention can be performed at any temperature which is compatible with the process equipment and procedures. Typically the process of the present invention can be performed at temperatures less than about 95° C. Preferably it can be performed in the range of about 20° C. to about 95° C., preferably about 20° C. to about 90° C., and more preferably bout 20° C. to about 70° C. The data in Table 2 show the effect of temperature on the conversion under the condition of the present invention of nitrilotris (methylenephosphonic acid) starting material and the selectivity among the products of the formation of formylphosphonic acid product at 65° C. and 90° C. These data show that lowering the reaction temperature increases the selectivity of the process in forming formylphosphonic acid.

TABLE 2

| Time, min | Conversion[a] at 65° C. | Selectivity[b] at 65° C. | Conversion[a] at 90° C. | Selectivity[b] at 90° C. |
|---|---|---|---|---|
| 0 | 0 | | 0 | |
| 40 | | | 35.4 | 70.4 |
| 70 | 18.3 | 84.0 | | |
| 80 | | | 69.0 | 63.5 |
| 120 | | | 96.2 | 58.2 |
| 140 | 30.9 | 83.3 | | |

TABLE 2-continued

| Time, min | Conversion[a] at 65° C. | Selectivity[b] at 65° C. | Conversion[a] at 90° C. | Selectivity[b] at 90° C. |
|---|---|---|---|---|
| 236 | 52.4 | 75.3 | | |
| 318 | 64.9 | 78.4 | | |
| 456 | 87.4 | 73.0 | | |

Reaction conditions are described in Example 7.
[a]Conversion of nitrilotris(methylenephosphonic acid) to products.
[b]Selectivity in the formation of formylphosphonic acid.

In the process of the present invention, a variety of oxidants can be employed in the oxidizing gas. Preferred oxidants include $O_2$, nitrogen oxides such as nitrous oxide, singlet oxygen and ozone. Most preferably, the oxidant comprises $O_2$. The oxidizing gas of the instant invention can, for example, comprise substantially $O_2$ or it can comprise $O_2$ diluted with one or more other gases. An example of an oxidizing gas comprising $O_2$ which has been diluted with other gases is air.

The oxidant, for example $O_2$, can be present in the process of the present invention at a wide range of partial pressures. Preferably the oxidant is present at a partial pressure in the range of about 10 kPa to about 10,000 kPa.

The manner in which the aminomethylphosphonic acid derivative is contacted with the oxidizing gas and the catalyst can vary greatly. For example, the aminomethylphosphonic acid derivative can be placed in a closed container with some free space containing the oxidizing gas and shaken vigorously or agitated by stirring, or the oxidizing gas can be bubbled through a solution of aminomethylphosphonic acid derivative containing the catalyst, either through a straight tube or a tube with a fritted diffuser attached thereto. The contacting can also be accomplished in a continuous reactor, for example a tube reactor, packed with a heterogeneous catalyst. Thus the process of this invention can involve actively contacting effectively the oxidizing gas with a mixture of the aminomethylphosphonic acid derivative containing the catalyst as illustrated herein. As those skilled in the art would realize from the disclosures of the present invention, merely allowing a mixture of the aminomethylphosphonic acid derivative containing the catalyst to stand in contact with air under proper conditions would produce some of the desired product.

In a continuous or in a non-continuous reaction process, various reactor streams can be recycled for use in other parts of the process. For example, used catalyst or solvent can be separated from the reaction mixture and re-used in the process.

When the process of the instant invention is run in a batch mode, the weight ratio of the aminomethylphosphonic acid derivative to the catalyst can vary widely. Conveniently the weight ratio can be in the range of about 0.001 to about 100,000 or more. When the catalyst is a heterogeneous catalyst, the weight ratio of the heterogeneous catalyst to the aminomethylphosphonic acid derivative can conveniently be in the range of about 0.001 to about 1000 or more. More preferably, the weight ratio can range from about 0.1 to about 100, and still more preferably from about 0.5 to about 50. When the catalyst is a homogeneous catalyst, the weight ratio of the homogeneous catalyst to the aminomethylphosphonic acid derivative can conveniently be in the range of about 0.1 to about 100,000 or more. More preferably, the weight ratio can range from about 1 to about 10,000, and still more preferably from about 50 to about 10,000. In a continuous reactor weight ratios of catalyst to the aminomethylphosphonic acid derivative can vary over even greater ranges than herein set forth.

Whether the reaction is carried out in a batch or continuous mode, reaction between the substrate and the reagent is preferably terminated at or prior to reaching a residual substrate concentration in the reaction mixture at which the rate of consumption of formylphosphonic acid exceeds the rate of formation of formylphosphonic acid. More preferably, the reaction between the substrate and reagent is terminated at an end point at which at least 75% of said substrate charged to the reaction zone has been converted to formylphosphonic acid and not more than 50% of the formylphosphonic acid so produced has been consumed by any further reaction. The reaction may be quenched, for example, by lowering the temperature of the reaction mixture to a temperature at which consumption of formylphosphonic acid essentially ceases. When operated in a continuous reaction zone into which said substrate and said reagent are continuously or intermittently introduced and from which a reaction product mixture comprising formylphosphonic acid is continuously or intermittently withdrawn, the residence time in said reaction zone is preferably controlled so that at least 75% of said substrate has been converted to formylphosphonic acid and not more than 50% of the formylphosphonic acid so produced has been consumed by any further reaction.

In one aspect of the present invention, $R^1$ and $R^2$ of the aminomethylphosphonic acid derivative of formula (II) are H. In another aspect, $R^4$ and $R^5$ of formula (II) are —$CH_2PO(OR^6)(OR^7)$, where $R^6$ and $R^7$ are as defined above. Preferably, $R^6$ and $R^7$ are H. In yet another aspect of the present invention, one of $R^4$ or $R^5$ of formula (II) is hydrocarbyl or substituted hydrocarbyl.

The process of the present invention can be performed in the presence of a solvent. Any solvent can be used which is compatible with the process equipment and procedures. In some embodiments of the instant invention the solvent can comprise water, an alcohol, a polyalcohol (such as ethylene glycol,) a polyether (such as polyethylene glycol), acetic acid, tetrahydrofuran, dioxane, or a mixture thereof. Preferably, the solvent is water. Preferably, the solvent comprises a hydroxyl-containing compound.

In one embodiment, the catalyst is a homogeneous catalyst comprising a transition metal, preferably a salt or an oxide of a transition metal. The transition metal can, for example, be vanadium, manganese, cobalt, ruthenium, or mixtures thereof. If the homogeneous catalyst comprises a vanadium salt, it is preferably vanadium sulfate, vanadium bromide, vanadium chloride, or vanadium acetylacetonate. Alternatively, the homogeneous catalyst can be a vanadium oxide such as vanadium pentoxide.

If the homogeneous catalyst comprises a manganese salt, it is preferably manganese acetate, manganese acetylacetonate, manganese iodide, manganese bromide, manganese chloride, manganese carbonate, manganese nitrate, or manganese sulfate. As an alternative, the homogeneous catalyst can be a manganese oxide such as manganese dioxide.

It is possible for the homogeneous catalyst of the present invention to comprise a cobalt salt. Preferred cobalt salts include cobalt sulfate, cobalt chloride, cobalt bromide, cobalt acetylacetonate, cobalt nitrate, and cobalt acetate. Cobalt oxides can also be used as homogeneous catalysts, for example cobalt (II) oxide or cobalt (III) oxide.

Ruthenium salts or ruthenium oxides can also be used as homogeneous catalysts in the inventive process. For example the ruthenium salt can be ruthenium acetylacetonate, ruthenium chloride, ruthenium bromide, ruthenium (III) oxide, or ruthenium (IV) oxide.

In the presence of a homogeneous catalyst, the process of the present invention can be performed at any temperature which is compatible with the process equipment and procedures. Typically, higher temperatures cause the process to run at higher reaction rates than do lower temperatures. In contrast, the process exhibits higher selectivity for the formylphosphonic acid derivative product at lower temperatures than it does at higher temperatures. Preferably the process of the present invention can be performed in the range of about 0° C. to about 150° C., preferably about 10° C. to about 95° C., and more preferably about 25° C. to about 75° C.

In a particularly preferred embodiment, the present invention provides a method for preparing formylphosphonic acid (formula IV), its esters, salts, acetals, hemiacetals, or hydrate, wherein the method comprises contacting nitrilotris (methylenephosphonic acid) (formula V), its esters, or its salts, with an oxidizing gas, at a temperature in the range of about 20° C. to about 150° C., in a reaction mixture under neutral or acidic conditions, in the presence of a heterogeneous catalyst for the oxidation of nitrilotris(methylenephosphonic acid), its esters, or its salts to form formylphosphonic acid, its esters, salts, acetals, hemiacetals, or hydrate. For the purposes of this invention, the hydrate of formylphosphonic acid is represented by the structure in which the aldehyde group is hydrated with water to form the gem-diol (i.e., $R^3$ of formula (I) is —CH(OH)$_2$). When $R^3$ of formula (I) is —CH(OR$^8$)(OR$^9$), wherein $R^8$ and $R^9$ are independently hydrocarbyl, substituted hydrocarbyl, or heterocycle, then formula (I) represents an acetal of formylphosphonic acid. When $R^3$ of formula (I) is —CH(OR$^8$)(OR$^9$), and one of $R^8$ or $R^9$ is H and the other of $R^8$ or $R^9$ is hydrocarbyl, substituted hydrocarbyl, or heterocycle, then formula (I) represents a hemiacetal of formylphosphonic acid.

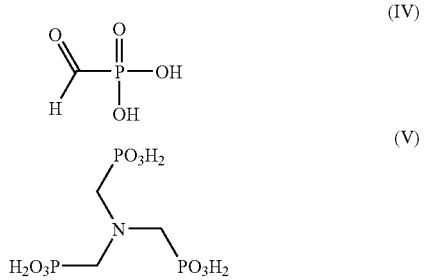

In an alternative embodiment, a formylphosphonic acid derivative and an amine are prepared from an aminomethylphosphonic acid derivative, with the subsequent regeneration of the aminomethylphosphonic acid derivative from the amine by phosphonomethylation. This embodiment recycles the amine, resulting in a reduced amount of wasted material. Eq. 2 shows an example of the instant process including a regeneration stage. In Eq. 2, $R^1$, $R^2$, $R^3$, $R^4$, $R^5$, $R^8$, and $R^9$ are as defined above. The phosphonomethylation regeneration stage can be in a single step or it can be in more than one step. Preferably, the formylphosphonic acid derivative and an amine are prepared by contacting oxygen, an aminomethylphosphonic acid derivative, and a suitable catalyst in a reaction mixture to produce a formylphosphonic acid derivative and an amine, with subsequent regeneration of the aminomethylphosphonic acid derivative from the amine. More preferably, the aminomethylphosphonic acid derivative is regenerated by contacting the amine, formaldehyde, and phosphorous acid. Alternatively, the aminomethylphosphonic acid derivative is regenerated by contacting the amine, formaldehyde, phosphorus trichloride and water. Conditions for the preparation of aminomethylphosphonic acid derivatives from amines by phosphonomethylation include, but are not limited to, those described in Moedritzer and Irani, J. Org. Chem., 31:1603 (1966), which is herein incorporated by reference. U.S. Pat. No. 3,738,937 also describes conditions for the preparation of aminomethylphosphonic acid derivatives from amines which can be used in the regeneration step of the instant invention and is herein incorporated by reference.

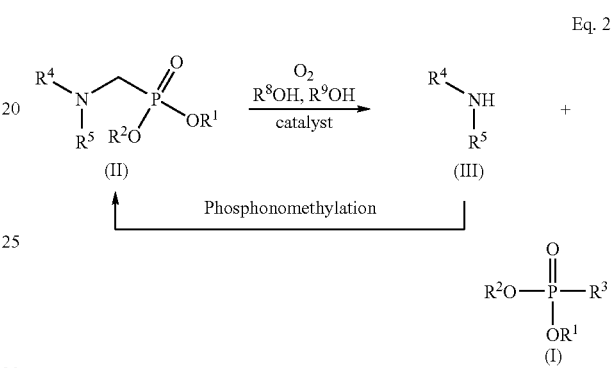

The products of the inventive process can be isolated from the reaction mixture by conventional methods or they can be used for purposes without isolation from the reaction product mixture.

In a preferred embodiment, the product of the inventive process is a precursor for producing other phosphorus species. For example, the inventive process may be further utilized as the first step in a multi-stage preparation of N-(phosphonomethyl)amino compounds (formula (IX) wherein $R^{10}$ can be H, hydrocarbyl, substituted hydrocarbyl, or heterocycle), or salts or esters thereof. An aminomethylphosphonic acid derivative having formula (II) can be contacted with an oxidizing gas and water, an alcohol, or a phenol in the presence of a catalyst for the oxidation of the aminomethylphosphonic acid derivative to produce a formylphosphonic acid derivative having formula (I). The resulting formylphosphonic acid derivative can be contacted with an amino compound of formula (X), wherein $R^{10}$ is as defined above, to form a condensed intermediate. The condensed intermediate can be reduced to produce the N-(phosphonomethyl)amino compound, or a salt, or an ester thereof. Examples of conditions under which the formylphosphonic acid derivative can be contacted with an amino compound, particularly glycine, to form a condensed intermediate which is reduced to produce an N-(phosphonomethyl)amino compound are described in U.S. Pat. No. 4,568,432, herein incorporated by reference. The reduction of the formed condensed intermediate to the N-(phosphonomethyl)amino compound or its salts or its esters can comprise, if desired, hydrogenation. In a preferred aspect of the present invention, the formylphosphonic acid derivative can be formylphosphonic acid or its hydrate. In a still more preferred aspect of the present invention, the amino compound is glycine or a salt or ester thereof. When the amino compound is glycine and the formylphosphonic acid derivative is formylphosphonic acid or its hydrate, the N-(phosphonomethyl)amino compound is N-(phosphonomethyl)glycine (formula (VI)). In another preferred embodiment of the present invention, the amino compound is 2-aminoethanol. When the amino compound is 2-aminoethanol and the formylphosphonic acid derivative is formylphosphonic acid or its hydrate, the N-(phosphonomethyl)amino compound product is N-(2-hydroxyethyl)-N-(phosphonomethyl)amine (formula (VII)). In yet another preferred embodiment, the amino compound is a source of ammonia, such as ammonia gas, ammonium hydroxide, an ammonium salt, or urea. When the amino compound is a source of ammonia and the formylphosphonic acid derivative is formylphosphonic acid or its hydrate, the N-(phosphonomethyl)amino compound product is aminomethylphosphonic acid (formula (VIII)).

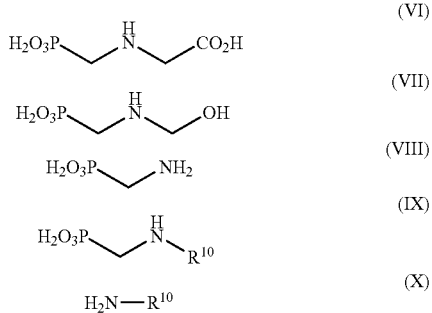

As a further aspect of the present invention a composition useful for the preparation of a formylphosphonic acid derivative having the formula (I) is now disclosed. The inventive composition comprises an aminomethylphosphonic acid derivative having the formula (II), an oxidizing gas, and a catalyst for the oxidation of the aminomethylphosphonic acid derivative to the formylphosphonic acid derivative.

The following non-limiting examples serve to illustrate the various aspects of the present invention. However, those of skill in the art should, in light of the present disclosure, appreciate that many changes can be made in the specific embodiments which are disclosed and still obtain a like or similar result without departing form the spirit and scope of the invention.

Detailed Preparative Methods

The starting materials for use in the methods of preparation of the invention are known or can be prepared by conventional methods known to a skilled person or in an analogous manner to processes described in the art.

Generally, the process methods of the present invention can be performed as follows.

Materials. Nitrilotris(methylenephosphonic acid) (ATMP) was isolated from commercially available aqueous solutions (Aldrich Chemical, Milwaukee, Wis.) by concentration and crystallization from 6-10 M HCl. Fresh HPL carbon catalyst represents activated carbon prepared by the methods outlined in example 4 of Chou (U.S. Pat. No. 4,624,937). Norit SX Plus and Norit SA-3 are commercially available from American Norit Co., Jacksonville, Fla. Norit SX Plus is an acid washed, steam activated powdered carbon with 96% of particles being smaller than 150 microns, and a surface area of 1000 m$^2$/g. Norit SA-3 is a steam activated carbon with 97% of particles being smaller than 150 microns, and a surface area of 750 m$^2$/g. All other chemicals were obtained from commercial sources and used without further purification.

Analysis. All formylphosphonic acid (FPA) analyses, unless otherwise indicated, were performed by $^{31}$P{$^1$H} NMR on a Varian Unity 300 at 121.4 MHz using a delay, dl, of 5 seconds. All NMR spectra were obtained from D$_2$O or H$_2$O/D$_2$O solutions. Chemical shifts are reported in ppm with $^{31}$H and $^{13}$C peaks reported as positive values downfield from sodium 3-(trimethylsilyl)-1-propanesulfonic acid (DSS) used as an internal standard and $^{31}$P chemical shifts are reported as positive values downfield from 85% H$_3$PO$_4$.

Synthesis. The tertiary phosphonomethyl amines N-methylimino-bis(methylenephosphonic acid) (NMI), N-cyclohexyl iminobis(methylenephosphonic acid), glyphosine and N-isopropyliminobis(methylenephosphonic acid) were prepared according to the method described by Moedritzer and Irani, *J. Org. Chem.* 31:1603(1966).

Phosphonomethylation of ethanolamine. Ethanolamine hydrochloride (50.24 g, 0.515 mol) and about 15 mL of water were placed in a 1000 mL round bottom flask. A solution of phosphorous acid (84.5 g, 1.03 mol) in 100 mL of water was added to the amine hydrochloride slurry along with 100 mL of concentrated HCl. The mixture was heated to reflux and aqueous formaldehyde (37%, 168.5 g, 2.07 mol) was added dropwise over 45 minutes. The completed mixture was held at reflux an additional 1 hour and then let cool to ambient temperature overnight. $^{31}$P NMR analysis of the crude material, concentrated to thick syrup by rotary evaporation, revealed an approximate 1.1 mixture of the cyclic and open form of N-(2-hydroxyethyl)iminobis(methylenephosphonic acid) (HEIB). Dissolving the crude syrup in methanol followed by cooling to 0° C. led to formation of a white precipitate that was isolated by filtration, washed with methanol, and dried in vacuo at 50° C. to afford 50.4 g of white crystals. The combined filtrate and methanol washes were let stand and afforded a second crop of white material that was similarly treated to yield an additional 28.8 g. Both crops were found to consist of 96 wt % cyclic HEIB and 4 wt % HEIB by $^{31}$P NMR. The total isolated yield was 66.4%. Cyclic HEIB (major): $^1$H NMR (D$_2$O, 300 MHz)δ 4.42 (dt, J$_{HP}$=13.0 Hz, 2H, —CH$_2$OP), 3.60 (unresolved, 2H, COPCH$_2$—), 3.57 (d, J$_{HP}$=12.7 Hz, 2H, —CH$_2$PO$_3$H$_2$); $^{31}$P NMR (D$_2$O, 121.4 MHz) 8.10 (dd, J$_{HP}$=12.98 Hz, Jpp=2.5 Hz, pendant P), 5.42 (apparent quint, J$_{HP,PP}$~12.6 Hz, ring P); $^{13}$C{$^1$H} (D$_2$O, 75.4 MHz) 61.8 (d, J$_{CP}$=4.9 HZ), 54.3 (dd, J$_{CP}$=138.3 and 7.7 Hz), 54.2 (dd, J$_{CP}$=5.7 and 4.6 Hz), 50.8 (dd, J$_{CP}$=128.8 and 4.0 Hz). Open HEIB (minor): $^{31}$P (D$_2$O, 121.4 MHz)9.02(t,J$_{HP}$=13.0 Hz).

Oxidation Apparatus. Reactions were performed in a stainless steel autoclave consisting of an 300-mL 316-stainless steel reactor equipped with all stainless steel wetted parts manufactured by Autoclave Engineers (Erie, Pa.). Oxygen was introduced into the reactor via sintered metal frit below a standard six-bladed radial impeller turning at 900 rpm. Oxygen was metered into the vessel using a Porter oxygen mass flow controller and reactor pressure was maintained by a research control valve controlled by the computer interface to regulate exit flow and maintain the specified reactor pressure. Gas flow exiting the reactor was monitored by a Porter mass flow meter.

EXAMPLE 1

Oxidation of nitrilotris(methylenephosphonic Acid)

Nitrilotris(methylenephosphonic acid) (25.00 g, 83.60 mmol), 2.63 g of HPL activated carbon catalyst, and 150 mL of water was charged to a 300-mL stainless steel autoclave. The oxidation was performed at 75° C. and 65 psig oxygen pressure using an oxygen flow rate of 38 sccm through the autoclave. After 81 minutes, analysis of the filtered reaction mixture by 31P{1H} NMR revealed 90% conversion of the nitrilotris(methylenephosphonic acid) starting material with an 82% selectivity to formylphosphonic acid. The amine co-product was iminobis(methylenephosphonic acid) with lesser amounts of N-formyliminobis(methylenephosphonic acid), phosphoric acid, and traces of phosphorous acid. Formylphosphonic acid: $^1$H NMR (300 MHz, D$_2$O)δ 5.26(d, $J_{HP}$=8 HZ); $^{31}$P NMR(121.4 MHz, H$_2$O/D$_2$O)δ 16.1 ppm(d, $J_{HP}$=8 Hz)

EXAMPLE 2

Temperature and Catalyst Comparison

The following reactions were carried out as described in Example 1, except as indicated in Table 3. The results summarized in Table 3 compare the effect of temperature and catalyst choice on conversion and selectivity to FPA. All conversion and selectivity data were obtained by $^{31}$P{$^1$H}NMR on filtered aliquots of the product mixture.

TABLE 3

Examples of ATMP oxidations with various
i. carbon catalysts and at different temperatures

| Catalyst | Temperature, ° C. | Reaction time, minutes | Conversion, % | FPA selectivity, % | FPA yield, % |
|---|---|---|---|---|---|
| HPL | 65 | 146 | 91 | 88 | 80 |
| HPL | 85 | 60 | 97 | 73 | 71 |
| Norit SX Plus | 75 | 300 | 63 | 69 | 43 |
| Norit SA-3 | 75 | 300 | 73 | 70 | 51 |

EXAMPLE 3

Oxidation of N-methyliminobis(methylene-phosphonic acid)

A 300-mL stainless steel autoclave was charged with N-methyliminobis(methylenephosphonic acid) (18.36 g, 83.81 mmol), 164 mL water, and 1.54 g of previously-used HPL carbon catalyst. The oxidation was carried out at 75° C. and pressure of 65 psig with an oxygen flow of 38 sccm into the rapidly stirred autoclave. After 240 minutes, the filtered reaction product was analyzed as described above. Results revealed a 24% conversion of starting material with a selectivity of 69% for FPA. The amine co-product was N-methyliminomethylenephosphonic acid.

EXAMPLE 4

Oxidation of isopropyliminobis(methylene-phosphonic acid)

A reaction was carried out as described in Example 3 using N-isopropyliminobis(methylenephosphonic acid) (15.00 g, 60.70 mmol), 160 mL water, and 1.44 g of previously-used HPL carbon catalyst. After 294 min, the filtered reaction product was analyzed as described in Example 1. Results revealed a 58% conversion of starting material with a selectivity of 76% for FPA. The major amine co-product was N-isopropylimino(methylenephosphonic acid).

EXAMPLE 5

Oxidation with Homogeneous Catalysis

Nitrilotris(methylenephosphonic acid) (25.0 g, 83.6 mmol), deionized water (150 g), and vanadyl sulfate hydrate (27.6 wt % H$_2$O), 0.33 g, 1.5 mmol) were charged to a 300 mL stainless steel autoclave. The mixture was pressurized to 65 psig with nitrogen and heated to 75° C. with mechanical stirring at 900 rpm. When the reaction temperature was reached, oxygen was sparged through the solution at 38 sccm for 50 minutes. Analysis of the product showed 94% conversion of the starting material with about 32% selectivity to FPA. The secondary amine co-product of the oxidation was iminobis(methylene-phosphonic acid) with N-formyliminobis(methylenephosphonic acid), H$_3$PO$_3$ and H$_3$PO$_4$ also noted.

EXAMPLE 6

Comparison of Acid and Base Conditions

The reactions were carried out as described in Example 1, except as indicated in Table 1. Acid or base was added to the reaction vessel at the start of the reaction. The results summarized in Table 1 demonstrate the effect of added equivalents of acid or base and the effect of pH on conversion of nitrilotris(methylenephosphonic acid) and yield of FPA under aqueous conditions. All conversion and yield data were obtained by $^{31}$P{$^1$H}NMR on filtered aliquots of the product mixture.

EXAMPLE 7

Effect of Temperature

The reactions were carried out as described in Example 1, except as indicated in Table 2. The results summarized in Table 2 demonstrate the effect of temperature on conversion of nitrilotris(methylenephosphonic acid) and selectivity of the reaction to produce FPA. All conversion and selectivity data were obtained by $^{31}$P{$^1$H}NMR on filtered aliquots of the product mixture.

EXAMPLE 8

Effect of Temperature and Time

Into a 300 mL Hastelloy C autoclave equipped with Hastelloy C wetted parts was charged 25.0 g of nitrilotris(methylenephosphonic acid), 2.63 g of HPL activated carbon, and 150 mL of water. The vessel was pressurized to 65 psig with nitrogen and heated to 115° C. Oxygen was then introduced at 90 sccm. Analysis of the filtered reaction product by $^{31}$P NMR after 35 minutes of oxygen flow at 115° C. revealed 96% conversion of the starting material with 42% selectivity to FPA for an FPA yield of 40%. The reaction was repeated as described above but at 95° C. Analysis of an aliquot of the filtered reaction mixture after 46 minutes revealed 92% conversion with 64% selectivity for an FPA yield of 58%. The reaction was again repeated but at 75° C. Analysis of an aliquot of the filtered reaction mixture after 132 minutes revealed 93% conversion with 75% selectivity for an FPA yield of 70%.

All of the compositions and methods disclosed and claimed herein can be made and executed without undue experimentation in light of the present The examples herein can be performed by substituting the generically or specifically described reactants and/or operating conditions of this invention for those used in the preceding examples. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention and are intended to be included within the scope of the following claims.

What is claimed is:

1. A method for producing N-(phosphonomethyl) glycine, a salt or ester thereof, the method comprising contacting formaldehyde, phosphorous acid and an amine, or a salt thereof, having the formula (III):

(III)

wherein
   $R^4$ and $R^5$ are independently selected from the group consisting of H, —CH$_2$PO(OR$^6$)(OR$^7$), hydrocarbyl, substituted hydrocarbyl, and heterocycle; and
   $R^6$ and $R^7$ are independently selected from the group consisting of H, hydrocarbyl, substituted hydrocarbyl, heterocycle, and a salt-forming cation;
to produce a phosphonomethylation reaction product mixture containing an aminomethylphosphonic acid substrate, or a salt thereof, having the formula (II):

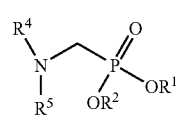

(II)

wherein
   $R^1$ and $R^2$ are independently selected from the group consisting of H, hydrocarbyl, substituted hydrocarbyl, heterocycle, and a salt forming cation; and
   $R^4$ and $R^5$ are as defined above;
contacting said aminomethylphosphonic acid substrate, or a salt thereof, having the formula (II), water and an oxidizing gas in the presence of a catalyst to form a formylphosphonic acid reaction product mixture containing formylphosphonic acid or a salt thereof and formic acid, and controlling the conditions under which said contacting is conducted so that (a) at least about 75% of the aminomethylphosphonic acid substrate is converted to formylphosphonic acid, or a salt thereof, (b) the molar ratio of formylphosphonic acid, or salt thereof, to formic acid is at least about 2:1 in said formylphosphonic acid reaction product mixture, and (c) no more than 50% of the formylphosphonic acid, or salt thereof formed in the formylphosphonic acid reaction product mixture is consumed therein; and
contacting said formylphosphonic acid with glycine in the presence of a reducing agent to produce a reductive alkylation reaction product mixture containing N-(phosphonomethyl) glycine, or a salt thereof.

2. The method of claim 1 wherein N-(phosphonomethyl) glycine, or a salt thereof is isolated from the reductive alkylation reaction product mixture.

3. The method of claim 1 wherein the pH of the formylphosphonic acid reaction product mixture is not less than about 1.5.

4. The method of claim 1 wherein the temperature of the formylphosphonic acid reaction product mixture is less than about 95° C.

5. The method of claim 1 wherein the catalyst comprises carbon impregnated with a noble metal.

6. The method of claim 5 wherein the noble metal is platinum or palladium.

7. A method for producing N-(phosphonomethyl) glycine, a salt or ester thereof, the method comprising contacting formaldehyde, phosphorous acid and an amine, or a salt thereof, having the formula (III):

(III)

wherein
   $R^4$ and $R^5$ are independently selected from the group consisting of H, —CH$_2$PO(OR$^6$)(OR$^7$), hydrocarbyl, substituted hydrocarbyl, and heterocycle; and
   $R^6$ and $R^7$ are independently selected from the group consisting of H, hydrocarbyl, substituted hydrocarbyl, heterocycle, and a salt-forming cation;
to produce a phosphonomethylation reaction product mixture containing an aminomethylphosphonic acid substrate, or a salt thereof, having the formula (II):

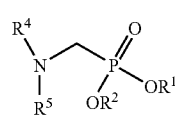

(II)

wherein
   $R^1$ and $R^2$ are independently selected from the group consisting of H, hydrocarbyl, substituted hydrocarbyl, heterocycle, and a salt forming cation; and $R^4$ and $R^5$ are as defined above;

contacting said aminomethylphosphonic acid substrate, or a salt thereof, having the formula (II), water and an oxidizing gas in the presence of a catalyst to form a formylphosphonic acid reaction product mixture containing formylphosphonic acid or a salt thereof, and controlling the conditions under which said contacting is carried out so that (a) at least about 75% of the aminomethylphosphonic acid substrate is converted to formylphosphonic acid, or a salt thereof, and (b) the yield of formylphosphonic acid, or salt thereof is at least 43%;

contacting said formylphosphonic acid with glycine to produce a condensation reaction product mixture containing a condensed intermediate; and reducing said condensed intermediate to produce a reduction product mixture containing N-(phosphonomethyl) glycine, or a salt thereof.

8. The method of claim 7 wherein N-(phosphonomethyl) glycine, or a salt thereof is isolated from the condensation reaction product mixture.

9. The method of claim 7 wherein the pH of the formylphosphonic acid reaction product mixture is not less than about 1.5.

10. The method of claim 7 wherein the temperature of the formylphosphonic acid reaction product mixture is less than about 95° C.

11. The method of claim 7 wherein the formylphosphonic acid reaction product mixture further contains formic acid and the molar ratio of formylphosphonic acid, or salt thereof, to formic acid is at least about 2:1 in said formylphosphonic acid reaction product mixture.

12. The method of claim 7 wherein the catalyst comprises carbon impregnated with a noble metal.

13. The method of claim 12 wherein the noble metal is platinum or palladium.

14. A method for producing N-(phosphonomethyl) glycine, a salt or ester thereof, the method comprising contacting formaldehyde, phosphorous acid and an amine, or a salt thereof, having the formula (III):

(III)

wherein $R^4$ and $R^5$ are independently selected from the group consisting of H, —CH$_2$PO(OR$^6$)(OR$^7$), hydrocarbyl, substituted hydrocarbyl, and heterocycle; and $R^6$ and $R^7$ are independently selected from the group consisting of H, hydrocarbyl, substituted hydrocarbyl, heterocycle, and a salt-forming cation;

to produce a phosphonomethylation reaction product mixture containing an aminomethylphosphonic acid substrate, or a salt thereof, having the formula (II):

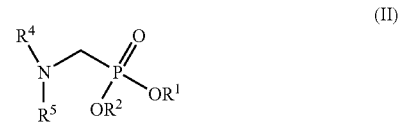

(II)

wherein $R^1$ and $R^2$ are independently selected from the group consisting of H, hydrocarbyl, substituted hydrocarbyl, heterocycle, and a salt forming cation; and $R^4$ and $R^5$ are as defined above;

contacting said aminomethylphosphonic acid substrate, or a salt thereof, having the formula (II), water and an oxidizing gas in the presence of a catalyst to form a formylphosphonic acid reaction product mixture containing formylphosphonic acid or a salt thereof, and controlling the conditions under which said contacting is carried out so that (a) at least about 75% of the aminomethylphosphonic acid substrate is converted to formylphosphonic acid, or a salt thereof, and (b) the yield of formylphosphonic acid, or salt thereof is at least 43%; and contacting said formyl phosphonic acid with glycine in the presence of a reducing agent to produce a reductive alkylation reaction product mixture containing N-(phosphonomethyl) glycine, or a salt thereof.

15. The method of claim 14 wherein N-(phosphonomethyl)glycine, or a salt thereof is isolated from the reductive alkylation reaction product mixture.

16. The method of claim 14 wherein the pH of the formylphosphonic acid reaction product mixture is not less than about 1.5.

17. The method of claim 14 wherein the temperature of the formylphosphonic acid reaction product mixture is less than about 95° C.

18. The method of claim 14 wherein the formylphosphonic acid reaction product mixture further contains formic acid and the molar ratio of formylphosphonic acid, or salt thereof, to formic acid is at least about 2:1 in said formylphosphonic acid reaction product mixture.

19. The method of claim 14 wherein the catalyst comprises carbon impregnated with a noble metal.

20. The method of claim 19 wherein the noble metal is platinum or palladium.

\* \* \* \* \*